(12) United States Patent
Matsuo et al.

(10) Patent No.: US 7,635,185 B2
(45) Date of Patent: Dec. 22, 2009

(54) FATIGUE RELIEF SUPPORTING APPARATUS

(75) Inventors: Kiyoshi Matsuo, Nagano (JP); Masao Yamamoto, Tokyo (JP)

(73) Assignee: Scalar Corporation, Tokyo (JP)

( * ) Notice: Subject to any disclaimer, the term of this patent is extended or adjusted under 35 U.S.C. 154(b) by 143 days.

(21) Appl. No.: 10/593,250

(22) PCT Filed: Mar. 17, 2005

(86) PCT No.: PCT/JP2005/005464

§ 371 (c)(1), (2), (4) Date: May 11, 2007

(87) PCT Pub. No.: WO2005/087158

PCT Pub. Date: Sep. 22, 2005

(65) Prior Publication Data

US 2007/0273827 A1 Nov. 29, 2007

(30) Foreign Application Priority Data

Mar. 17, 2004 (JP) ............................. 2004-077120

(51) Int. Cl.
*A61B 9/00* (2006.01)
(52) U.S. Cl. ...................................................... 351/203
(58) Field of Classification Search ................ 351/205, 351/206, 210, 212, 218, 221, 203, 245
See application file for complete search history.

(56) References Cited

U.S. PATENT DOCUMENTS 5,813,990 A * 9/1998 Ryll ............................. 600/500
6,394,601 B1 * 5/2002 Bettinger ...................... 351/158

FOREIGN PATENT DOCUMENTS

| JP | 51940/1992 | 5/1992 |
|---|---|---|
| JP | 6-12766 Y2 | 4/1994 |
| JP | 3002145 U | 9/1994 |
| JP | 373/1996 | 2/1996 |
| JP | 10-33583 A | 2/1998 |
| JP | 11-47208 A | 2/1999 |
| JP | 11-56942 A | 3/1999 |
| JP | 3063648 U | 11/1999 |
| JP | 2000-157586 A | 6/2000 |
| JP | 2002-350790 A | 12/2002 |
| JP | 2004-236241 A | 8/2004 |

OTHER PUBLICATIONS

International Search Report.
English Language Abstracts of JP 11-56942A; JP 2000-157586A; JP2002-350790A; JP3063648U; JP10-33583A; JP4-51940U; JP2004-236241A; JP6-12766Y2; JP11-47208A; JP3002145U; JP8-373U.

* cited by examiner

*Primary Examiner*—Ricky L Mack
*Assistant Examiner*—Tuyen Q Tra
(74) *Attorney, Agent, or Firm*—Paul, Hastings, Janofsky & Walker LLP

(57) ABSTRACT

The present invention provides a technique for enabling a user of a personal computer, a television, or the like to relieve his or her fatigue without difficulties. The present invention provides a fatigue relief supporting apparatus wherein the apparatus has image generating means for generating an image of a predetermined object which shuttles on a screen of an image display device in a horizontal direction and displaying the object image on the screen of the image display device, and wherein the user looks down to follow the object image with the user's eyes to relieve the user's fatigue.

16 Claims, 12 Drawing Sheets

FATIGUE RELIEF SUPPORTING APPARATUS

TECHNICAL FIELD

The present invention relates to a fatigue relief supporting apparatus that relieves a user's fatigue.

BACKGROUND OF THE INVENTION

Recently prevailing personal computers and word processors are commonly used for work over an extended period of time.

Television games have been more frequently played at home, resulting in the long use of televisions.

However, viewing a display screen of a personal computer, a television, or the like for an extended period of time significantly reduces the motion of eyeballs to impose a heavy burden on a user viewing the display screen; the user is fatigued.

An example of a conventional method for relieving the burden, that is, the fatigue involves turning the user's eyes away from the display screen and seeing remote sights. However, this method may be impossible depending on the environment in which the personal computer, television, or the like is installed.

The present invention is made in view of these problems. An object of the present invention is to provide a technique that enables a user of a personal computer, television, or the like to relieve his or her fatigue without difficulties.

DISCLOSURE OF THE INVENTION

The present invention provides a fatigue relief supporting apparatus comprising a main body that can be worn on a user's head, and a display member for displaying a predetermined object image, said display member being provided on or in said main body in such a manner that it is not very clearly visible for said user when said user wearing said main body on his or her head looks straight ahead, and that it becomes clearly visible for said user when said user moves his or her eyes down, the apparatus offers good visibility for said user when said user wearing said main body on user's head looks straight ahead, wherein the apparatus has image generating means for generating an image of the object which shuttles in a horizontal direction with respect to the user and displaying the generated object image on the display member, the object image has a function that relieve his or her fatigue if the user looks down to follow the object image with the user's eyes.

With the fatigue relief supporting apparatus, the image generating means generates the predetermined object image shuttling in the horizontal direction with respect to the user and displays the generated object image on the display member.

The object image has a function that relieve his or her fatigue if the user looks down to follow the object image with the user's eyes. The use of the fatigue relief supporting apparatus thus enables the user's fatigue to be relieved.

The term "user's fatigue" as used in the specification refers to various symptoms such as headache, stiff shoulders, feeling of fatigue, dry eyes, and tinnitus which may occur when the user continuously views the display screen of a personal computer, a television, or the like.

The term "horizontal direction with respect to the user" as used in the specification refers to the direction that is substantially parallel to a straight line joining the user's right eye with his or her left eye.

Explanation will be given below of the reason why the user can relieve his or her fatigue by looking down to follow the predetermined object image with his or her eyes.

A user continuously viewing the display screen of a personal computer, a television, or the like is fatigued by the excessive tension of his or her sympathetic nerves.

The sympathetic nervous system is active during waking hours. It acts to use energy. The parasympathetic nervous system is active during sleep. It acts to conserve body energy. Stimulation of the parasympathetic nervous system results in low blood pressure, pupil constriction, slow heart rate and breathing, and increase in gastrointestinal motility. On the contrary, sympathetic stimulation results in high blood pressure, pupil dilation, fast heart rate and breathing, and decrease in gastrointestinal motility One's upward looking at something (with his or her face facing the front) above his or her horizontal line of sight activates the sympathetic nervous system. On the other hand, one's downward looking at something (with his or her face facing the front) below his or her horizontal line of sight activates the parasympathetic nervous system.

As apparent from the above, one can activate his or her parasympathetic nervous system by looking at something below his or her horizontal line of sight, thereby to achieve a relaxed state.

The user can relieve his or her fatigue by looking down and following the object image displayed on the display member by the image generating means of the fatigue relief supporting apparatus of the present invention. Accordingly, watching the object activates the parasympathetic nerves forcibly. The fatigue relief supporting apparatus of the present invention thus enables the user to be relaxed to ease and prevent symptoms such as headache and stiff shoulders. In other words, the fatigue relief supporting apparatus of the present invention can relieve the user's fatigue.

Any display member may be used provided that it can display the object image. For example, the display member may be a liquid crystal display.

The present invention also provides a fatigue relief supporting apparatus comprising a main body that can be worn on a user's head, and a light emitting section having a plurality of light emitting members arranged in a line (for example, linearly), said light emitting member being provided on or in said main body in such a manner that it is not very clearly visible for said user when said user wearing said main body on his or her head looks straight ahead, and that it becomes clearly visible for said user when said user moves his or her eyes down, the apparatus offers good visibility for said user when said user wearing said main body on user's head looks straight ahead, wherein the apparatus has light emission signal generating means for generating a light emission signal that allows the plurality of light emitting members to emit light so that a light image obtained by allowing the plurality of light emitting members to sequentially emit light shuttles in a horizontal direction with respect to the user and allowing the plurality of light emitting members to emit light on the basis of the generated light emission signal, and the light image has a function that relieves his or her fatigue if the user looks down to follow the light image with the user's eyes.

The light image displayed on the light emitting section by the light emission signal generating means of the fatigue relief supporting apparatus of the present has a function that relieves his or her fatigue if the user looks down to follow the light image with the user's eyes. Accordingly, as is the case with the above fatigue relief supporting apparatus, watching the light image activates the parasympathetic nerves forcibly. The fatigue relief supporting apparatus of the present invention thus enables the user to be relaxed to ease and prevent symptoms such as headache and stiff shoulders.

According to the present invention, any light emitting members may be used provided that it can emit predetermined light. For example, LEDs or tip parts of optical fibers may be used as light emitting members.

Looking down are required to activate the parasympathetic nerves. But, if the display member or light emitting section provided on or in said main body in such a manner that it is not very clearly visible for said user when said user wearing said main body on his or her head looks straight ahead, which interferes with the user's daily life by cutting of the use's view. Accordingly, the display member may be provided in the main body so as to become clearly visible for said user only when said user moves his or her eyes down at an angle equal to or larger than 20 degrees. Likewise, the light emitting section may be provided in the main body so as to become clearly visible for said user only when said user moves his or her eyes down at an angle equal to or larger than 20 degrees.

This allows the user to naturally look down, when user watches the display member or light emitting section through downcast eyes. The parasympathetic nerves can thus be activated.

Both the display member and light emitting section may be provided so as to become clearly visible for said user only when said user moves his or her eyes down at an angle equal to or smaller than 70 degrees, though they should be provided so as to become clearly visible for said user only when said user moves his or her eyes down at an angle equal to or larger than 20 degrees as described above. This is because it is difficult for user to moves his or her eyes down at an angle equal to or larger than 70 degrees, and requesting the user to do that may result in his or her fatigue.

If the angle through which the user is requested to move down his or her eyes when looking at the display member or light emitting section is 45 degrees, the user is likely to be least fatigued. In consideration of this, the display member or light emitting section may be provided in the main body so as to become clearly visible for said user only when said user moves his or her eyes down at an angle equal to 45 degrees.

The term "downward (down)" as used herein includes both a frontward and downward direction and a laterally obliquely frontward and downward direction.

Both the display member and light emitting section have only to be provided in the main body in such a manner that they are not very clearly visible for said user when said user wearing said main body on his or her head looks straight ahead, and that they become clearly visible for said user when said user moves his or her eyes down.

That is to say, the display member may be united with the main body. The light emitting section may also be united with the main body. For example, the display member and light emitting section may be fitted into a part of the main body. Such a fatigue relief supporting apparatus does not require the display member or light emitting section to be mounted in the main body at the point of use of the apparatus and can thus be easily used. However, the display member or light emitting section may be removably attached to the main body at a predetermined position.

One or more display members may be provided. Similarly, one or more light emitting sections may be provided. For example, the display member may include a right-eye display member located below the user's right eye and a left-eye display member located below the user's left eye. Alternatively, the light emitting section may include a right-eye light emitting section located below the user's right eye and a left-eye light emitting section located below the user's left eye.

This enables the object image or the like to shuttle from one end such as the right-eye display member to the other end such as the left-eye display member. This apparatus enables the user's fatigue to be more effectively relieved than an apparatus with only one of the right-eye and left-eye display members or the like.

The object image displayed on the display member can shuttle in the horizontal direction with respect to the user. Further, the light image from the light emitting section can shuttle in the horizontal direction with respect to the user. For example, the display member may have a predetermined width and a predetermined length so that the object image can reciprocate along the length of the display member. The light emitting section may have a predetermined width and a predetermined length so that the light image can shuttle along the length of the light emitting section.

This enables a reduction in the width of the display member or light emitting section to make the configuration of the display member or light emitting section compact.

The image generating means may generate the object image such that the image makes a change that promotes the user to blink. The light emission signal generating means may generate the light image such that the image makes a change that promotes the user to blink.

The number of blinks decreases significantly when the user continuously views the display screen of a personal computer or the like over an extended period of time. The user is then likely to exhibit what is called a dry eye symptom. Thus, if the object image or light image makes a change that promotes the user to blink, the user can be promoted to blink. This makes it possible to prevent dry eyes.

Such an object image as makes a change that promotes the user to blink may be any image provided that it makes a change that promotes the user to blink. Such a light image as makes a change that promotes the user to blink may be any light image provided that it makes a change that promotes the user to blink.

To make a change in the object image which promotes the user to blink, it is possible to change the color or shape of at least a part of the object image or to blink the object image. Moreover, the movement speed or motion of the object image may be changed. Further, it is possible to display, in addition to the object image, an image containing characters such as "Please blink" which promote the user to blink. Alternatively, an image different from that of the object, for example, an image of blinking eyes, may be displayed.

Further, to make a change in the light image which promotes the user to blink, the light emitting section may be configured so that the light emission color of some of the plurality of light emitting members comprising the light emitting section differs from that of the other light emitting members. Then, when the former light emitting members, having the light emission color different from that of the latter light emitting members, emit light, the user is promoted to blink. Alternatively, the movement speed of the light image may be varied. Alternatively, a light emitting member to promote the user to blink may be provided which has a light emission color or light quantity different from that of the others so as to promote the user to blink when the light emitting member which has a light emission color or light quantity different from that of the others emits light.

The image generating means may generate the object image, for example, at predetermined timings at predetermined time intervals. Similarly, the light emission signal generating means may generate the light image, for example, at predetermined timings at predetermined time intervals.

This enables the user to view the object image or light image, for example, every time a predetermined time elapses.

According to the present invention, the main body may be arbitrarily shaped as long as the display member or light emitting section can be provided in or on the main body and the apparatus offers good visibility for said user when said user wearing said main body on user's head looks straight ahead.

The main body may be formed like, for example, glasses. The glasses shape in this case includes a goggle shape.

If the main body is shaped like glasses, it may comprise a glasses frame having a lower frame. In this case, the display member or light emitting section may be provided on the lower frame of the glasses frame.

Further, if the main body is shaped like glasses, the main body comprises glasses lenses. In this case, the display member or light emitting section can be provided on the lower frame of the glasses frame. If the display member includes right-eye and left-eye display members, the right-eye display member can be attached to the lower frame corresponding to the right eye. The left-eye display member can be attached to the lower frame corresponding to the left eye. If the light emitting section includes right-eye and left-eye light emitting sections, the right-eye light emitting section can be attached to the lower frame corresponding to the right eye. The left-eye light emitting section can be attached to the lower frame corresponding to the left eye. Of course, the glasses lenses in this case may or may not be of a prescription type. Furthermore, the glasses lenses corresponding to the right and left eyes may be connected together.

BEST MODE FOR CARRYING OUT THE INVENTION

Figure 1:
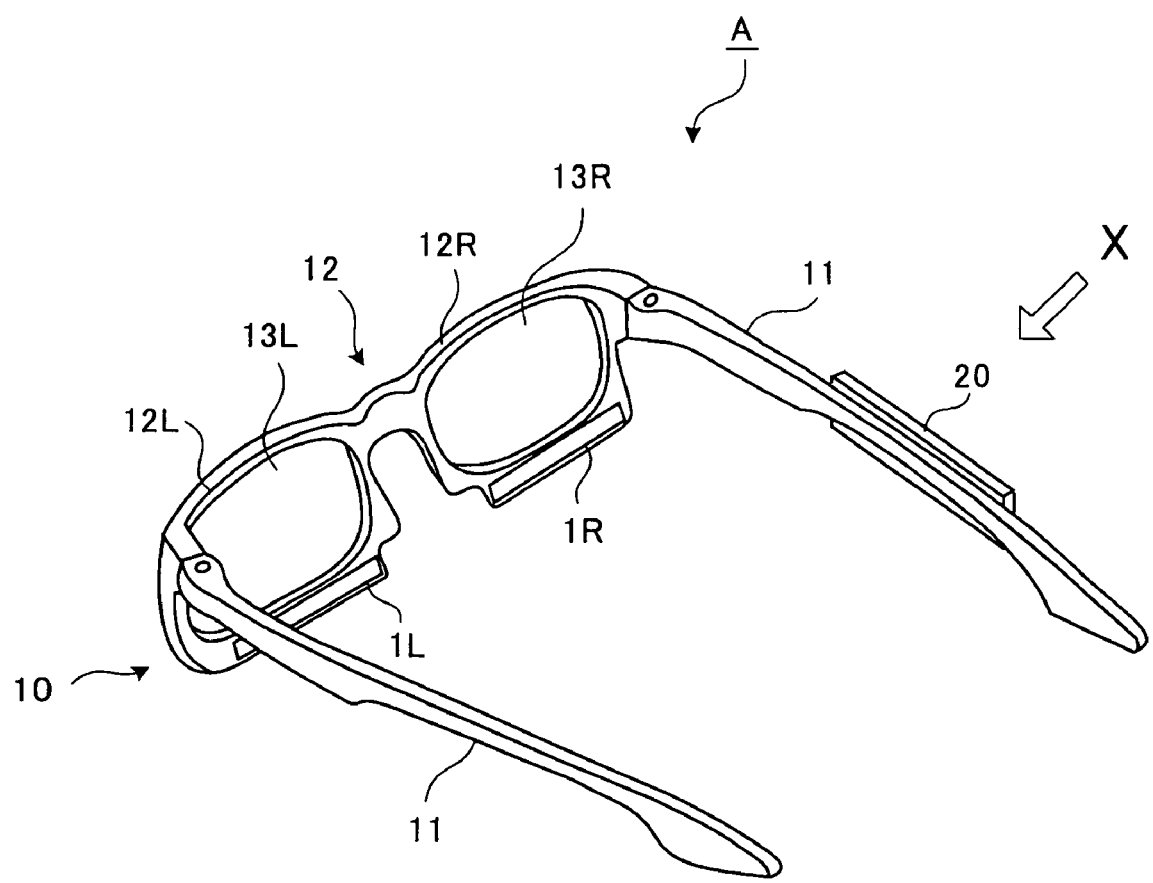
FIG. 1 is a perspective view showing an entire fatigue relief supporting apparatus according to a first embodiment as viewed from behind.

A preferred first to third embodiments of the present invention will be described below in detail with reference to the drawings.

In the description of the embodiments, common objects are denoted by the same reference numerals. Duplicate descriptions will be sometimes omitted.

First Embodiment

FIG. 1 is a perspective view showing an entire fatigue relief supporting apparatus A according to a first embodiment of the present invention as viewed from behind. In the description of the embodiments, the rear of the fatigue relief supporting apparatus means a side of the fatigue relief supporting apparatus A which sits closer to the user's face when the apparatus A is worn on the user's head.

The fatigue relief supporting apparatus A includes a main body 10, and a right-eye display 1R and a left-eye display 1L which display an object image.

The main body 10 according to this embodiment is shaped like a glasses frame and includes temples 11 and a frame 12, but is not limited to this.

That is to say, in use, the fatigue relief supporting apparatus A is fixedly worn on the user's head in a manner similar to that in which the user wears glasses. The two temples 11 of the main body 10 are placed around the user's ears to enable the fatigue relief supporting apparatus A to be fixedly worn on the user's head.

The frame 12 includes a right-eye frame 12R and a left-eye frame 12L. The right-eye frame 12R is the frame 12 located in front of the user's right eye when the fatigue relief supporting apparatus A is fixedly worn on the user's head. The left-eye frame 12L is the frame 12 located in front of the user's left eye when the fatigue relief supporting apparatus A is fixedly worn on the user's head. Although not always required, both frames 12 are substantially rectangular according to the present embodiment. The lower parts of both frames 12 are lower frames according to the present invention. The lower frames are formed to be slightly longer than side frames located at the opposite ends of the lower frames.

A right-eye lens 13R and a left-eye lens 13L are fitted inside the right-eye frame 12R and left-eye frame 12L according to this embodiment, respectively. Both the right-eye lens 13R and left-eye lens 13L are gently curved, colorless transparent glass plates of a non-prescription type. Of course, the right-eye lens 13R and left-eye lens 13L may be of a prescription type or may be colored or formed of a material other than glass, for example, resin. Further, the right-eye lens 13R and left-eye lens 13L may not be present.

Displays are fitted into the lower frames of the right-eye frame 12R and left-eye frame 12L to display an object image.

Specifically, a right-eye display 1R is set in the lower frame of the right-eye frame 12R. A left-eye display 1L is set in the lower frame of the left-eye frame 12L.

The right-eye display 1R and left-eye display 1L are set in the lower frames so that when the fatigue relief supporting apparatus A is fixedly worn on the user's head, a screen is located where the user can view it as shown in FIG. 1. The right-eye display 1R and left-eye display 1L are substantially rectangular and are appropriately sized to be set in the lower frame.

The present embodiment uses a liquid crystal display as a display.

With the fatigue relief supporting apparatus A fixedly worn on the user's head, the user can intentionally view an object image shown on the displays 1R and 1L as described later.

Since the right-eye display 1R and left-eye display 1L are attached to the lower frames of the right-eye frame 12R or left-eye frame 12L of the glasses frame-shaped main body 10, the right-eye display 1R and left-eye display 1L are not very clearly visible for said user as long as the user looks straight ahead.

That is to say, even with the fatigue relief supporting apparatus A worn on the head, the user can maintain as clear a vision as in the case in which the user wears ordinary glasses. As long as the user looks straight ahead, he or she can get a good visibility. In other words, even with the fatigue relief supporting apparatus A worn on the head, the user can view the screen of a personal computer or the like without any difficulties.

On the other hand, the user with the fatigue relief supporting apparatus A worn on his or her head can view the right-eye display 1R and left-eye display 1L by moving his or her eyes down. The user can thus view the object image shown on the displays 1R and 1L.

In this embodiment, when the user moves his or her eyes down at an angle 45 degrees from the condition in which the head faces frontward, the right-eye display 1R and left-eye display 1L become clearly visible. In other words, when the user moves his or her eyes down at an angle 45 degrees from the condition in which the head faces frontward, the user can view the object image shown in the right-eye display 1R and left-eye display 1L.

To offers good visibility for said user when user does not view the object image, the displays 1R and 1L have only to become clearly visible for said user only when said user moves his or her eyes down at an angle equal to or larger than 20 degrees. If this angle is too large, it becomes difficult to see the object image shown on the right-eye display 1R and left-eye display 1L. Accordingly, the displays 1R and 1L may be provided so as to become clearly visible for said user only when said user moves his or her eyes down at an angle equal to or smaller than 70 degrees.

The right-eye display 1R and left-eye display 1L are thus provided in the main body 10.

In the present embodiment, the right-eye display 1R and left-eye display 1L are set in the lower frames of the right-eye frame 12R and left-eye frame 12L. However, the present invention is not limited to this. The right-eye display 1R and left-eye display 1L may be attached to the bottoms of the lower frames.

The right-eye display 1R and left-eye display 1L are connected to a controller 20 attached to the temple 11 at a predetermined position via wiring (not shown).

The controller 20 operates and controls the right-eye display 1R and left-eye display 1L. In the present embodiment, the controller 20 is shaped like a substantial elongate rectangular parallelepiped and attached to the right-eye frame 12R-side temple 11 so as not to interfere with the wearing of the main body 10 on the user's head. However, the controller 20 may be shaped and positioned so as not to interfere with the wearing of the main body 10 on the user's head. For example, the controller 20 may be shaped and positioned so as to be used as the temples 11 of the main body 10.

Figure 4:
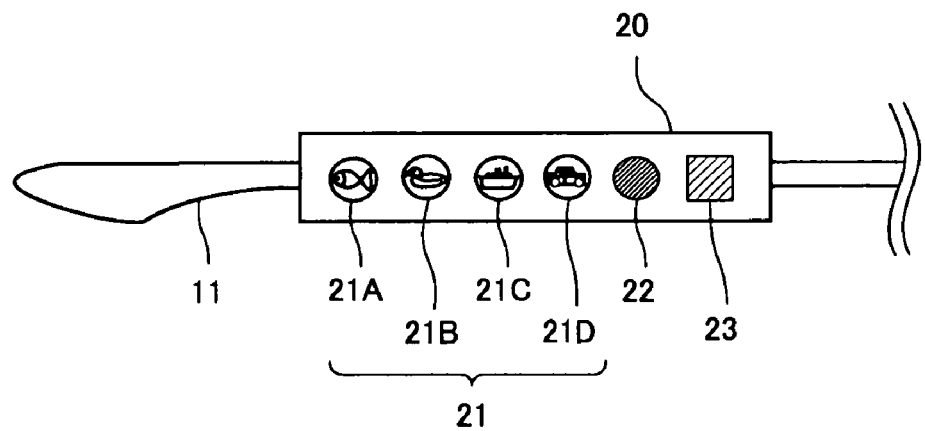
FIG. 4 is a diagram showing the controller for the fatigue relief supporting apparatus according to the first embodiment as viewed from an X direction in FIG. 1.

The controller 20 has operation buttons 21 arranged at predetermined positions on its surface as shown in FIG. 4.

The operation buttons 21 allow the user to select any one of a plurality of object data recorded in an object data recording section 61 described below. In the present embodiment, the operation buttons 21 are provided on an outer surface of the controller 20 which lies opposite its surface closer to the user's skin when the main body 10 is worn on the user's head.

Figure 2:
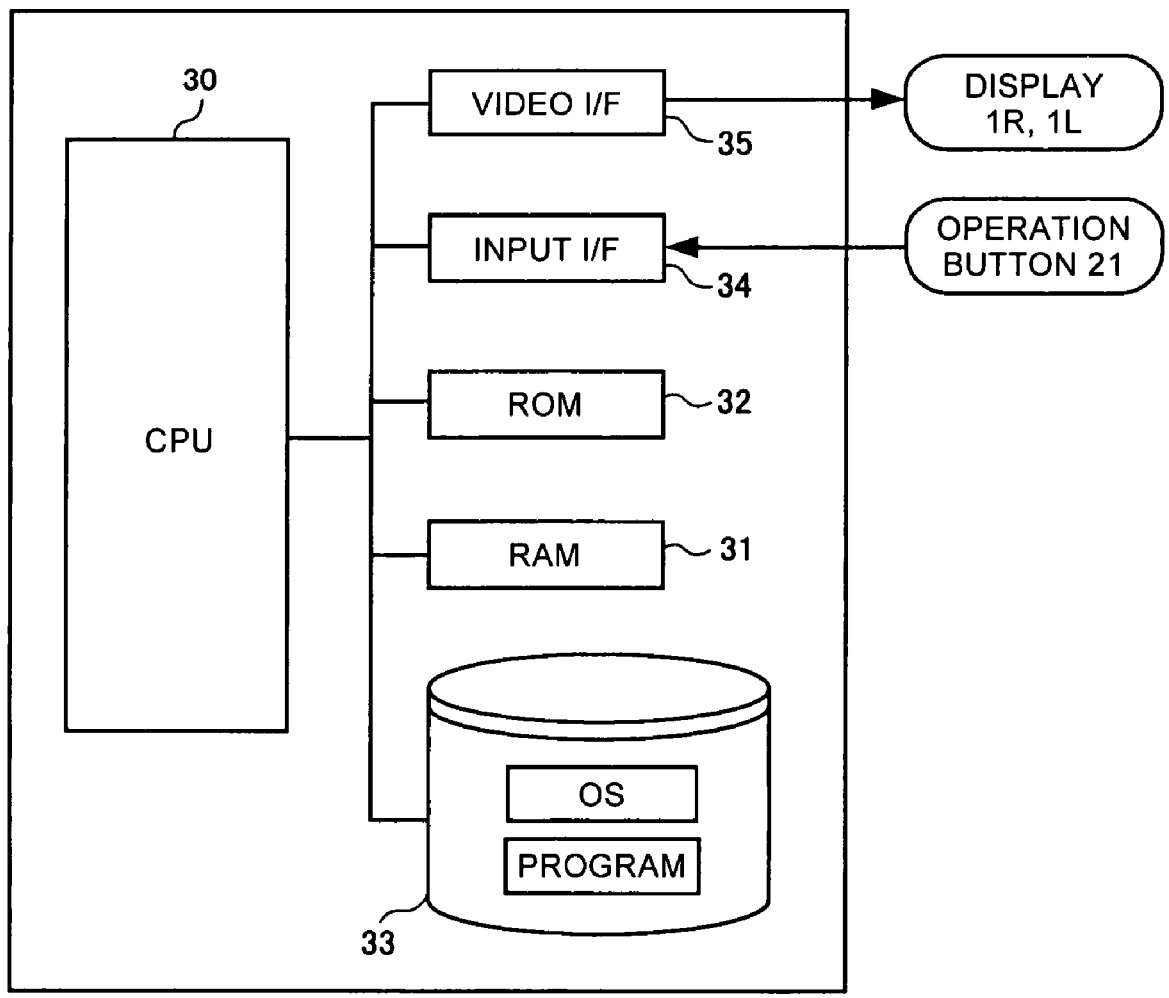
FIG. 2 is a diagram showing the configuration of a controller for the fatigue relief supporting apparatus according to the first embodiment.

As shown in FIG. 2, the controller 20 has a CPU 30 that controls the operation of the whole controller 20, a RAM 31 and a ROM 32 that are example of memories, and magnetic storage device 33, an input interface 34 via which an operation signal from the operation button 21 is input, and a video interface 35 for the right-eye display 1R and left-eye display 1L. An operation system (OS) is installed in the magnetic storage device 33.

The controller 20 has a predetermined control program pre-installed in its ROM 32 so as to operate fatigue relief supporting apparatus A as the fatigue relief supporting apparatus of the present invention.

The predetermined computer program allows the controller 20 connected to the right-eye display 1R and left-eye display 1L to function as display control means for generating an image of a predetermined object shuttling on the displays 1R and 1L in a horizontal direction with respect to the user and storage means for storing the object image. The computer program allows the light image to have a function that relieves his or her fatigue if the user looks down to follow the light image with the user's eyes.

The computer program may form functions required to allow the controller 20 to operate as the fatigue relief supporting apparatus A solo or may form the required function in cooperation with the OS mounted in the controller 20.

Figure 3:
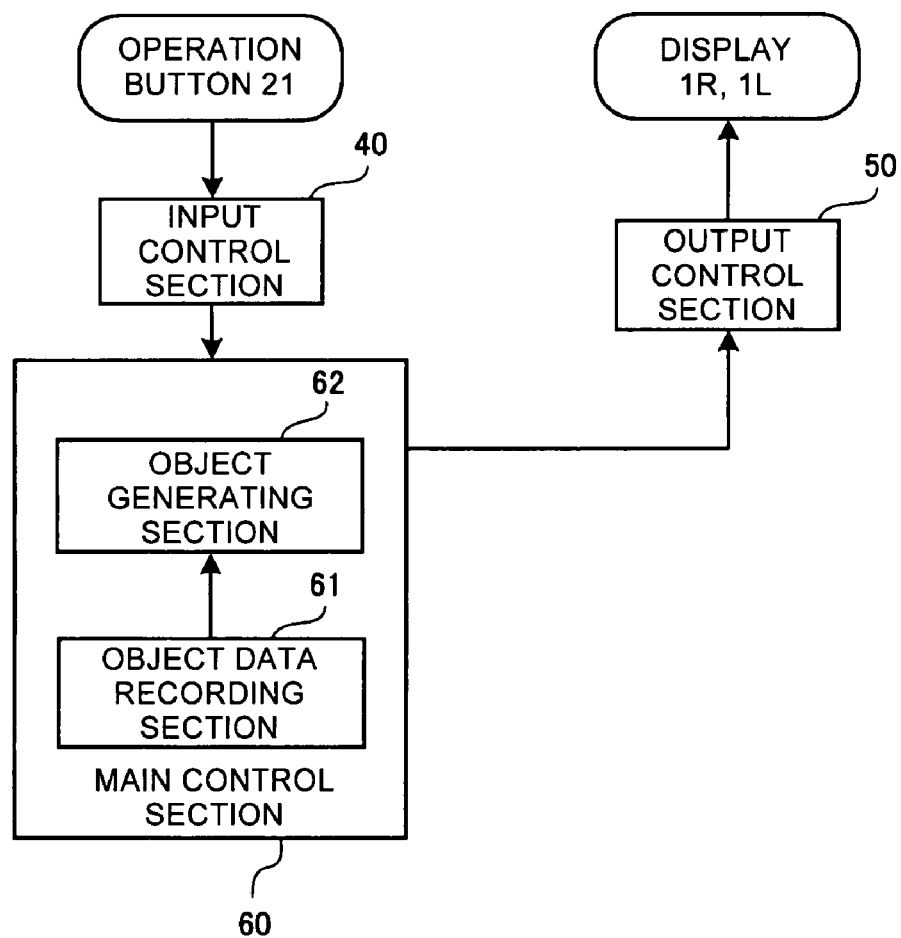
FIG. 3 is a diagram showing the configuration of the fatigue relief supporting apparatus according to the first embodiment.

In the present embodiment, the installed computer program is read in the RAM 31 and executed by the CPU 30 to form the functions shown in FIG. 3, on the controller 20. Specifically, the functions of an input control section 40, an output control section 50, and a main control section 60 are formed to constitute the fatigue relief supporting apparatus A.

The input control section 40 executes control to accept an input via the operation button 21 and to provide it to the main control section 60.

The output control section 50 executes control to output data to the displays 1R and 1L. When an object image described below is generated, the output control section 50 displays it on the displays 1R and 1L.

The main control section 60 integrally controls the whole fatigue relief supporting apparatus A. The input control section 40 and output control section 50 operate under the control of the main control section 60.

The main control section 60 generates an object image. Specifically, the main control section 60 has an object data recording section 61 that records data on an object image (hereinafter referred to as object data) in a predetermined area of predetermined data recording means (not shown), and an object generating section 62 that reads out the object data recorded in the object data recording section 61 to generate an image.

Predetermined object data is recorded in the object data recording section 61. In the present embodiment, object data on four objects, a "goldfish", a "duck", a "ship", and a "car"

is recorded in the object data recording section 61. However, any number of types of object data may be recorded in the object data recording section 61. The more number of object data recorded, the more number of choices for an object image. This allows user to choose an object image that suits his or her taste and mood.

In the present embodiment, the object data is installed in the magnetic storage device 33 of the controller 20 simultaneously with the installation of the above computer program in the magnetic storage device 33.

The object generating section 62 generates an object image to be displayed on the displays 1R and 1L, on the basis of the object data.

The object image generated by the object generating section 62 is an image of the predetermined object shuttling on the screens of the displays 1R and 1L in the horizontal direction, that is, an image that shuttles in the horizontal direction with respect to the user when the fatigue relief supporting apparatus A is worn on the user's head. The user looks down to follow the object image with his or her eyes to relieve his or her fatigue. Further, in this embodiment, the image makes a change that promotes the user to blink.

The object generating section 62 has a timer (not shown) and can thus generate an image even after a predetermined time has elapsed.

FIG. 4 is a diagram showing the controller 20 as viewed from an X direction in FIG. 1. In other words, FIG. 4 shows the surface of the controller 20 on which the operation buttons 21 are provided.

The operation buttons 21 according to the present embodiment, for which the object data on the four objects, "goldfish", "duck", "ship", and "car" is recorded in the object data recording section 61 as described above, include four operation buttons 21A to 21D, as shown in FIG. 4. Images of the objects ("goldfish", "duck", "ship", and "car") recorded in the object data recording section 61 is drawn on the buttons. The buttons are associated with the object data on the respective objects.

This surface is also provided with an end button 22 that ends the display of the object image on the displays 1R and 1L and a power supply switch 23 serving as a power supply for the fatigue relief supporting apparatus A. The use of the fatigue relief supporting apparatus A requires the power supply switch 23 to be turned on.

Figure 5:
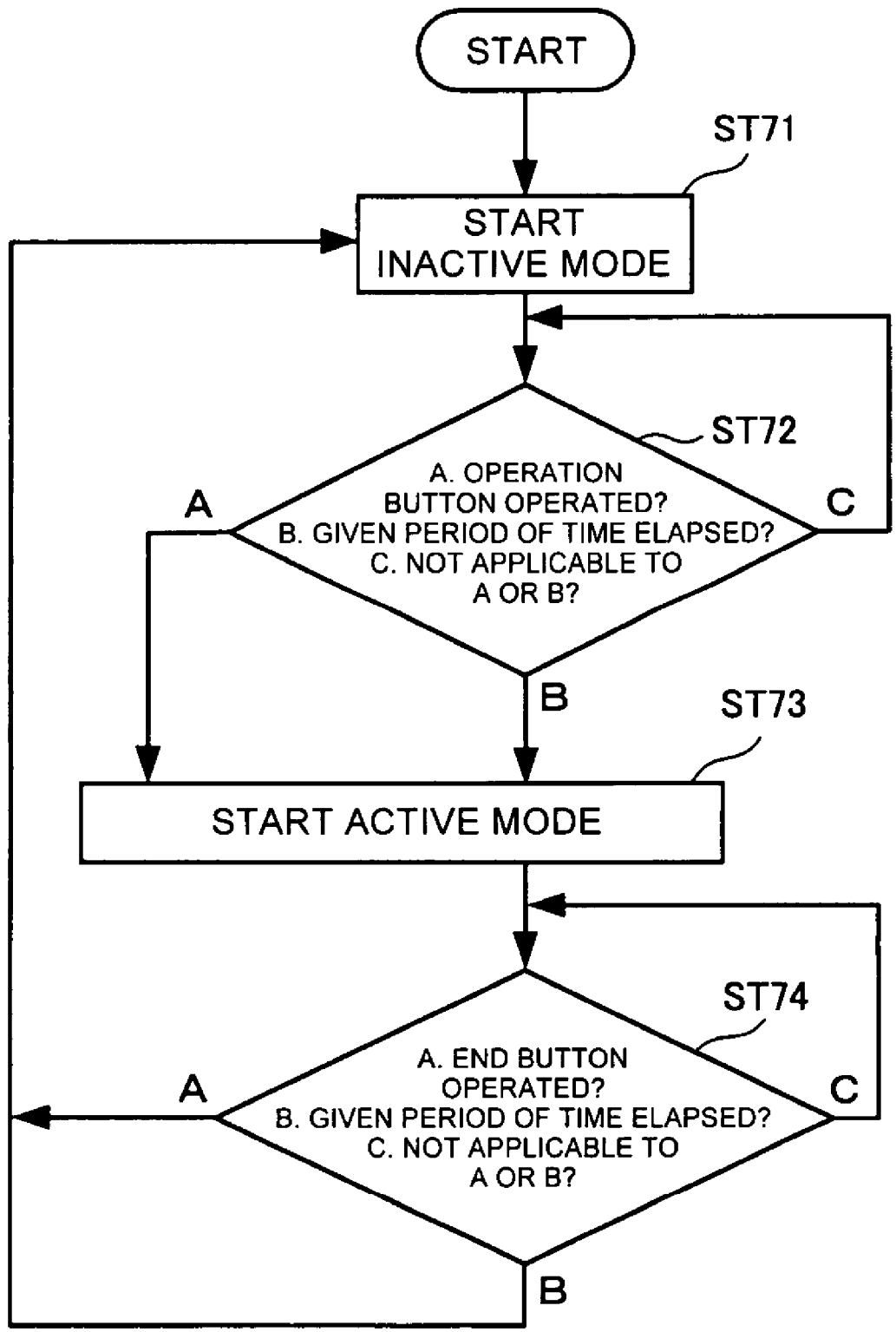
FIG. 5 is a flowchart illustrating the flow of a process in the fatigue relief supporting apparatus.

Now, with reference to the flowchart in FIG. 5, description will be given of operation procedure of the fatigue relief supporting apparatus A configured as described above.

The fatigue relief supporting apparatus A with the power supply switch 23 turned on has two modes, an inactive mode and an active mode.

In the inactive mode, the object image is not displayed on the right-eye display 1R or left-eye display 1L. In the active mode, the object image is displayed either on the right-eye display 1R or on the left-eye display 1L.

In the inactive mode, the main control section 60 controls the output control section 50 so that nothing is displayed on the displays 1R and 1L (ST71).

If the user operates (depresses) any one of the operation buttons 21 (ST72: A), the input control section 40 accepts data indicating that this operation has been performed. The input control section 40 then inputs the data to the main control section 60, which then changes the inactive mode to the active mode (ST73).

If a given period of time has elapsed without any input via the operation button 21 (ST72: B), the main control section 60 changes the inactive mode to the active mode (ST73). If the user does not operate the operation button 21 or the given period of time has not elapsed without the operation (ST72: C), the inactive mode continues (ST72).

The timer continuously monitors whether or not the given period of time has elapsed.

In the active mode, the main control section 60 generates a predetermined object image to be displayed on the displays 1R and 1L, on the basis of the input from the input control section 40. Specifically, this process is executed by the object generating section 62. That is to say, the object data generating section 62 generates an object image by reading data on an object selected by the user, the data being contained in the object data recorded in the object data recording section 61. For example, if the user depresses the operation button 21A for the "goldfish", the object generating section 62 generates an image of the "goldfish" object.

When the object image is generated, the main control section 60 controls the output control section 50 so that the generated object image is displayed on the displays 1R and 1L. The motion of the object image will be described below.

Figure 6:
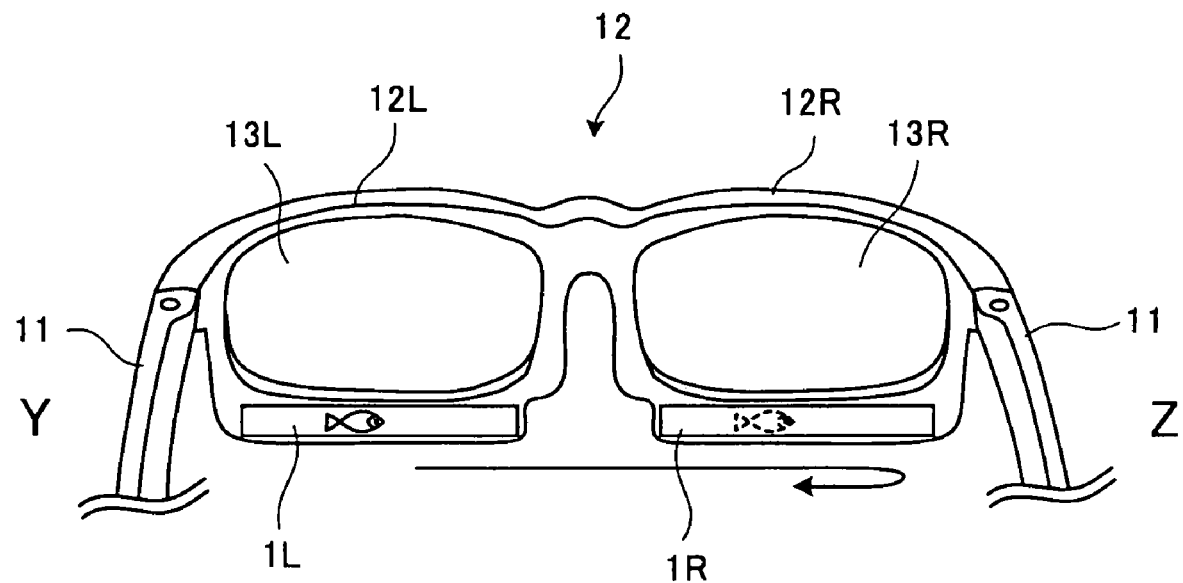
FIG. 6 is a diagram showing that an object image is displayed on a display.

FIG. 6 is a diagram showing that an image of a "goldfish" is shown in the displays 1R and 1L.

If the end button 22 on the controller 20 is operated by the user (ST74: A), the input control section 40 accepts this and inputs it to the main control section 60.

The main control section 60 thus controls the output control section 50 so that the display of the object image on the displays 1R and 1L is stopped. This changes the active mode to the inactive mode (ST71).

If a given period of time has elapsed since the start of display of the object image (ST74: B), the active mode also changes to the inactive mode (ST71).

If the user does not perform any operation or the given period of time has not elapsed yet since the start of display of the object image (ST74: C), the active mode continues (ST74). Whether or not the given period of time has elapsed is continuously monitored by the timer.

To end the use of the fatigue relief supporting apparatus A, the power supply switch 23 is turned off.

Now, description will be given of a method for using an object image shown on the displays 1R and 1L.

FIG. 6 is a diagram showing that an image of a "goldfish", an example of an object image, is shown in the displays 1R and 1L.

This object image, a goldfish shuttles on the screens of the displays 1R and 1L in the horizontal direction at a predetermined speed.

Specifically, as shown in FIG. 6, the goldfish moves from a side of the left-eye display 1L (Y side in the figure) on which the temple 11 of the left-eye display 1L is provided, toward the right-eye display 1R (Z side in the figure). Upon moving to the Z end on the left-eye display 1L screen, the goldfish disappears from the left-eye display 1L screen and appears at the Y end on the right-eye display 1R screen. The goldfish having appeared at the Y end on the right-eye display 1R screen moves toward the Z side and to the Z end. When the goldfish has moved to the Z end of the right-eye display 1R, it changes its direction and then moves to the Y end of the left-eye display 1L as described above.

Thus, if the goldfish moving on the screens of the displays 1R and 1L has moved to the end of each display 1R or 1L where the temple 11 is provided, it changes its direction to shuttle.

When the goldfish has moved to the end of each display 1R or 1L where the temple 11 is provided, it starts to blink.

The user follows the goldfish shown on the displays 1R and 1L with his or her eyes. The user also blinks in harmony with the blinking of the goldfish.

Figure 7:
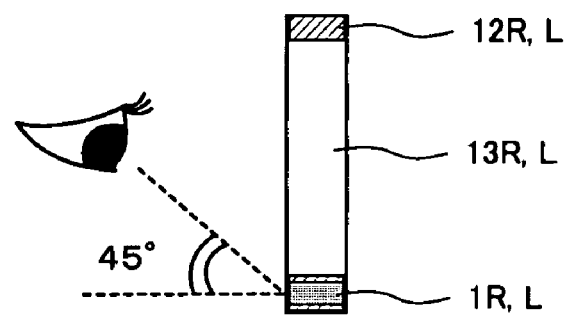
FIG. 7 is a diagram showing how to view the object image displayed on the display.

In this case, as shown in FIG. 7, the user watches the object image by moving his or her eyes (in the present embodiment, through 45 degrees). Accordingly, while the user is watching the object image, the parasympathetic nerves are activated to enable the user to be relaxed to relieve his or her fatigue.

Further, blinking of the goldfish promotes the user to blink to prevent dry eyes.

As described above, the user can relieve his or her fatigue by looking down to follow the object image shown on the screens of the displays 1R and 1L of the fatigue relief supporting apparatus A of the present invention. Consequently, while the user is watching the object image, the parasympathetic nerves are activated to ease the tension of the user's sympathetic nerves to relax him or her. This makes it possible to ease and prevent symptoms such as headache, stiff shoulders, feeling of fatigue, dry eyes, or tinnitus. In other words, the user's fatigue can be relieved.

In the present embodiment, the object image blinks when it has come to the end of each display 1R or 1L where the temple 11 is provided. However, the image has only to be an object shuttling on the screens of the displays 1R and 1L in the horizontal direction so that the user can look down to follow the image with his or her eyes to relieve his or her fatigue.

If the object image makes a change that promotes the user to blink, it is not limited to the one that blinks but may be configured as described below.

For example, the object image may at least partly change its color.

Figure 8:
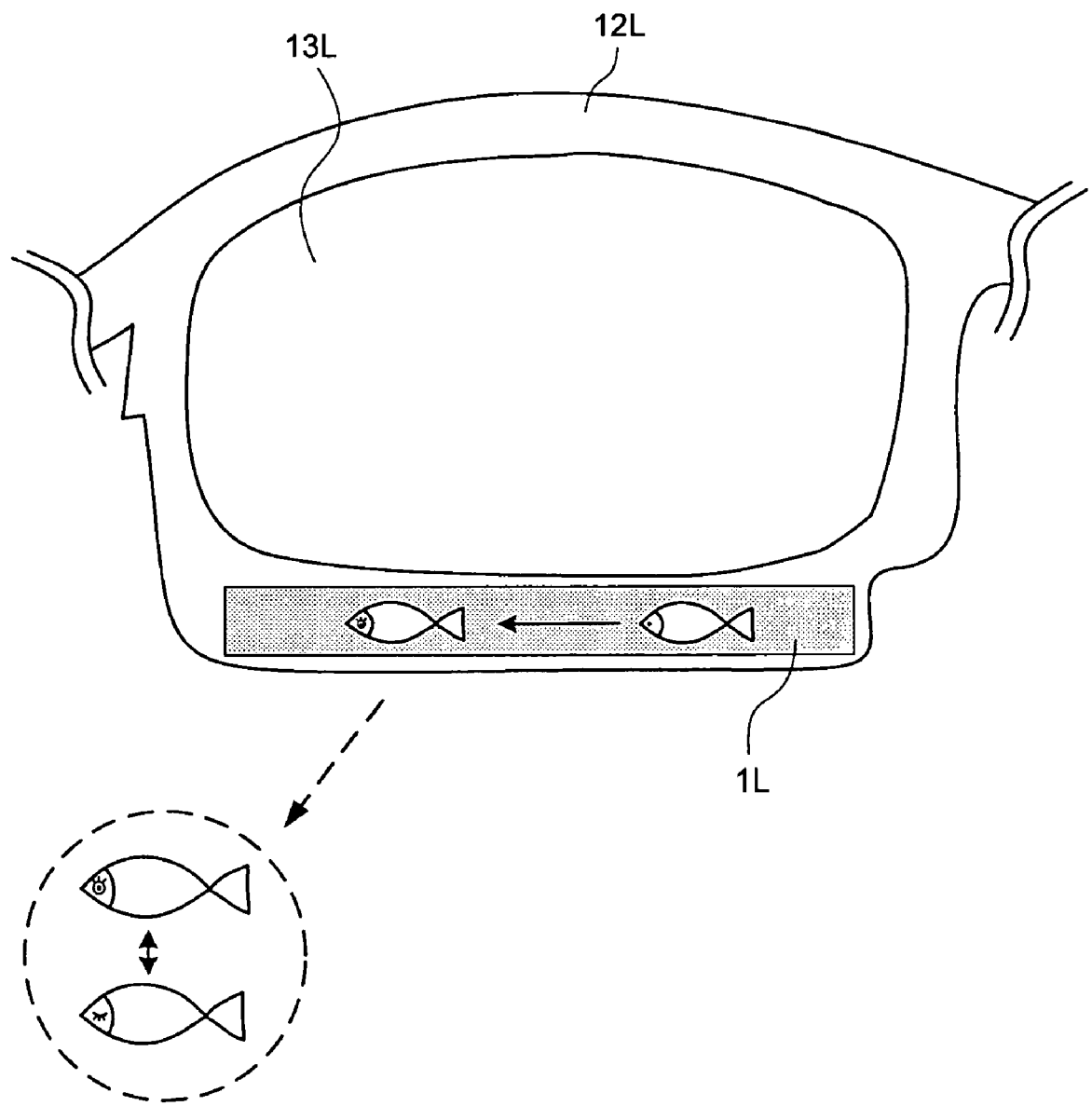
FIG. 8 is a diagram showing an exemplary display of the object image.

Alternatively, the movement speed, motion, or size of the object image may be changed. Specifically, as shown in FIG. 8, the goldfish may blink when its image has moved to the end of each display 1R or 1L where the temple 11 is provided.

Figure 9:
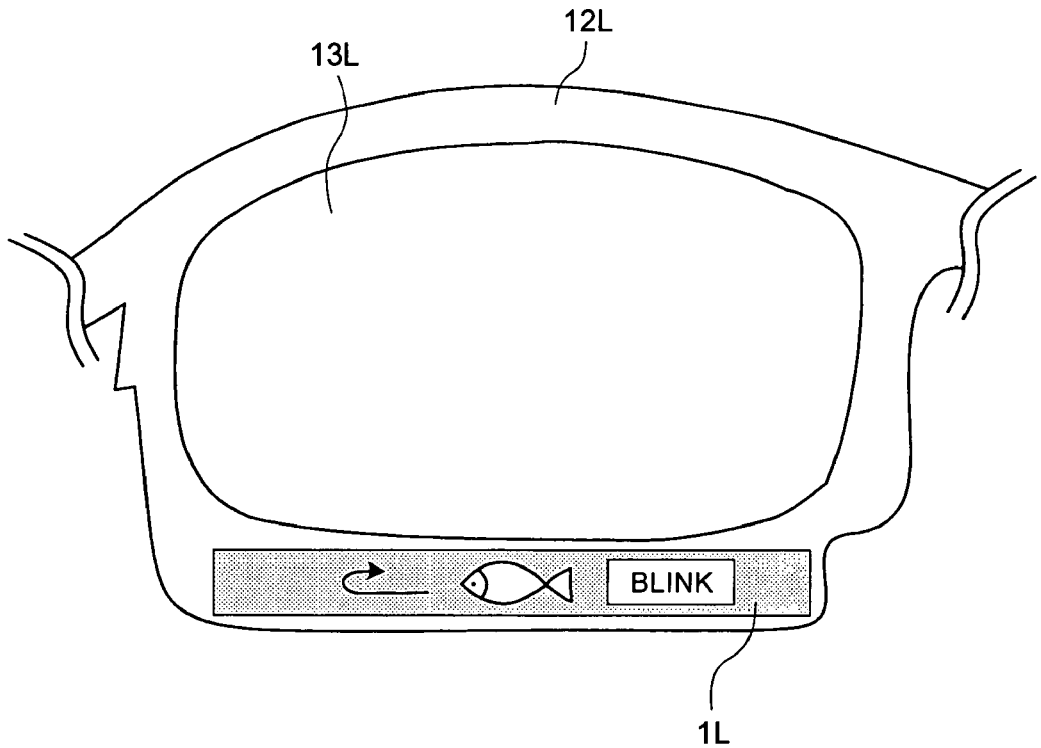
FIG. 9 is a diagram showing an exemplary display of the object image.
Figure 10:
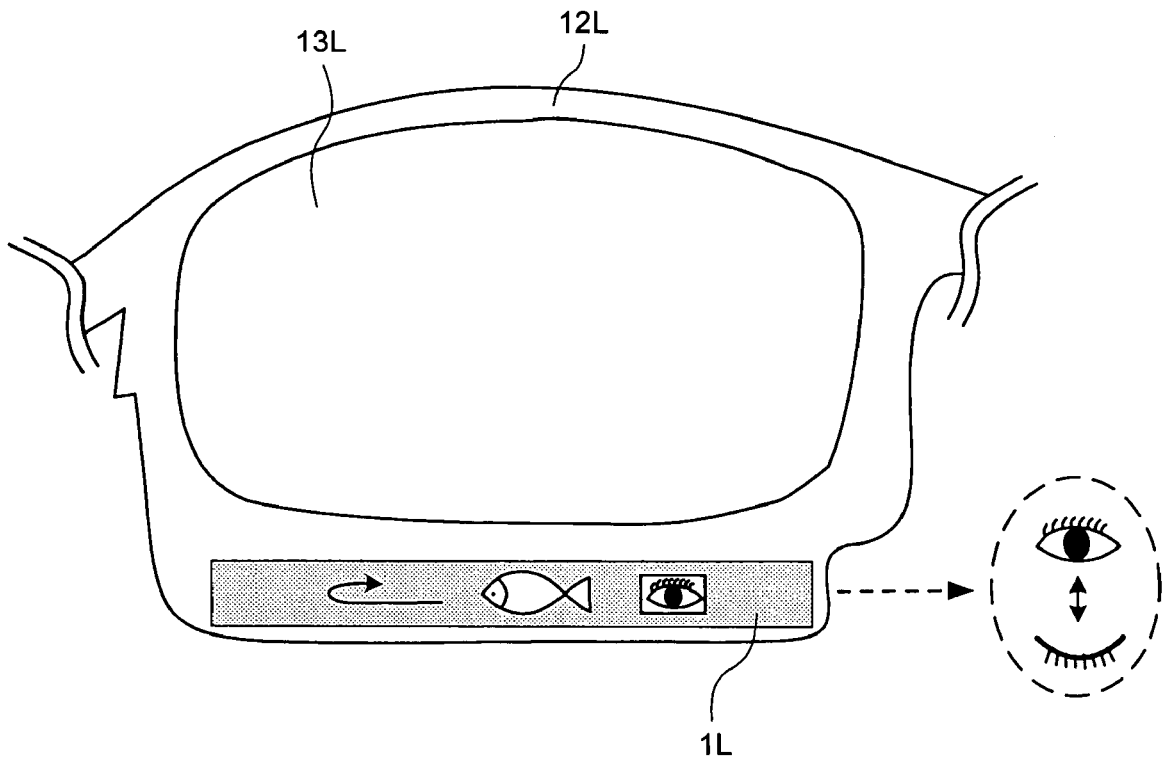
FIG. 10 is a diagram showing an exemplary display of the object image.

Alternatively, as shown in FIG. 9, in addition to the object image, an image containing characters such as "blink" which promote the user to blink may be displayed. Alternatively, an image of a blinking eye may be displayed as shown in FIG. 10. These images may be displayed anywhere on the display 1R or 1L.

Moreover, in the present embodiment, the generated object image is alternately displayed on the right-eye display 1R and left-eye display 1L. However, the object image may be displayed on only one of the right-eye display 1R and left-eye display 1L. In this case, the user may select either the right-eye display 1R or left-eye display 1L, or the main control section 60 may arbitrarily select either the right-eye display 1R or left-eye display 1L. Alternatively, the object image may be displayed on each of the displays 1R and 1L.

This also applies to a second and third embodiments described later.

Second Embodiment

A fatigue relief supporting apparatus B according to the present embodiment is configured in substantially the same manner as that in which the fatigue relief supporting apparatus A according to the first embodiment is configured. The method of usage is also the same for both fatigue relief supporting apparatuses A and B. However, the fatigue relief supporting apparatus B is different from the fatigue relief supporting apparatus A in that the former includes a right-eye LED section 101R and a left-eye LED section 101L each having a plurality of LEDs 102, in place of the right-eye display 1R and left-eye display 1L. That is to say, the fatigue relief supporting apparatus B according to the present embodiment does not display any object image but a light image obtained by allowing the LED sections 101R and 101L to emit light.

Figure 11:
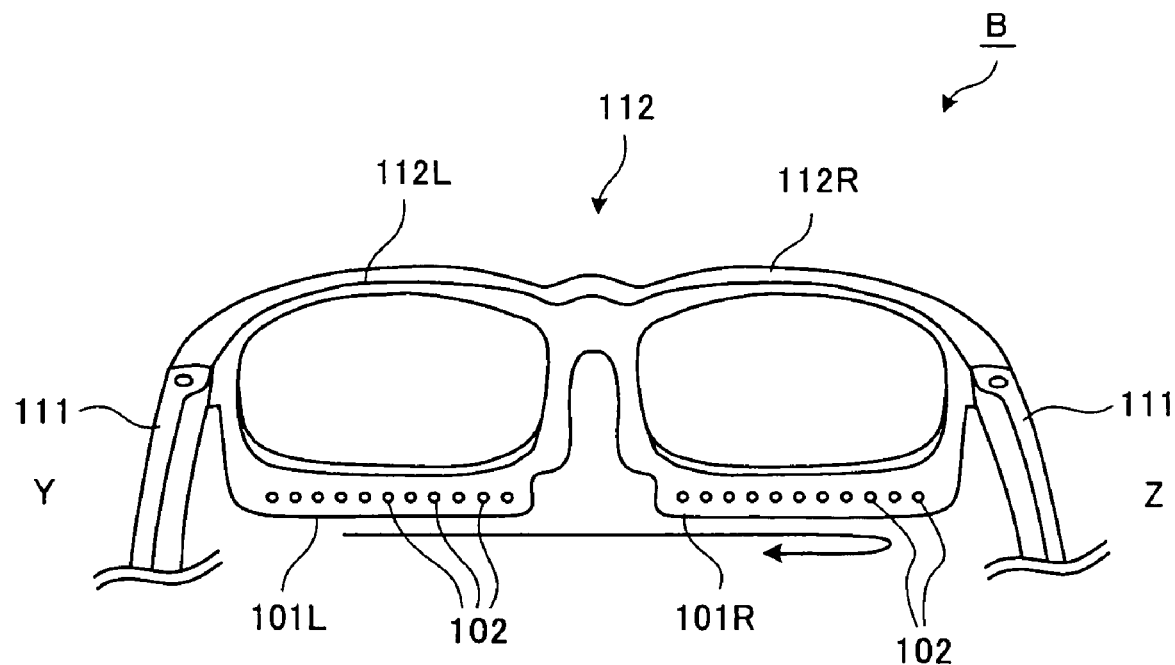
FIG. 11 is a diagram showing a fatigue relief supporting apparatus according to a second embodiment.

As shown in FIG. 11, the right-eye LED section 101R and left-eye LED section 101L consist of a plurality of LEDs 102 arranged and set in lower frames of a right-eye frame 112R and a left-eye frame 112L, respectively, in a longitudinal direction of the lower frames. The plurality of LEDs 102 are set in the lower frames so as to be visible to the user when the fatigue relief supporting apparatus B is fixedly worn on the user's head. The present embodiment uses the white LEDs 102.

In the present embodiment, as is the case with the fatigue relief supporting apparatus A according to the first embodiment, the right-eye LED section 101R and left-eye LED section 101L become clearly visible for user only when said user moves his or her eyes down at an angle equal to 45 degrees. The right-eye LED section 101R and left-eye LED section 101L are further connected to a controller 120 attached to a temple 111 at a predetermined position.

Figure 12:
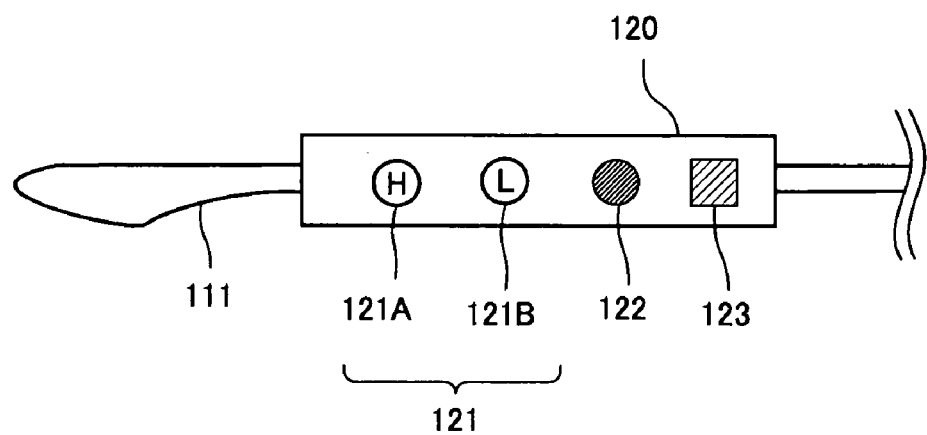
FIG. 12 is a diagram showing a controller for the fatigue relief supporting apparatus according to the second embodiment.

As shown in FIG. 12, the controller 120 is provided with an operation button 121, an end button 122, and a power supply switch 123, as is the case with the first embodiment.

The operation button 121 according to the present invention allows the user to select one of a plurality of light emission signal patterns recorded in a light emission signal pattern recording section 161 described later. The present embodiment provides two operation buttons 121; one 121A of the buttons is shown as "H", whereas the other button 121B is shown as "L". The "H" button is associated with a "High" light emission signal pattern described later. The "L" button is associated with a "Low" light emission signal pattern described later.

Figure 13:
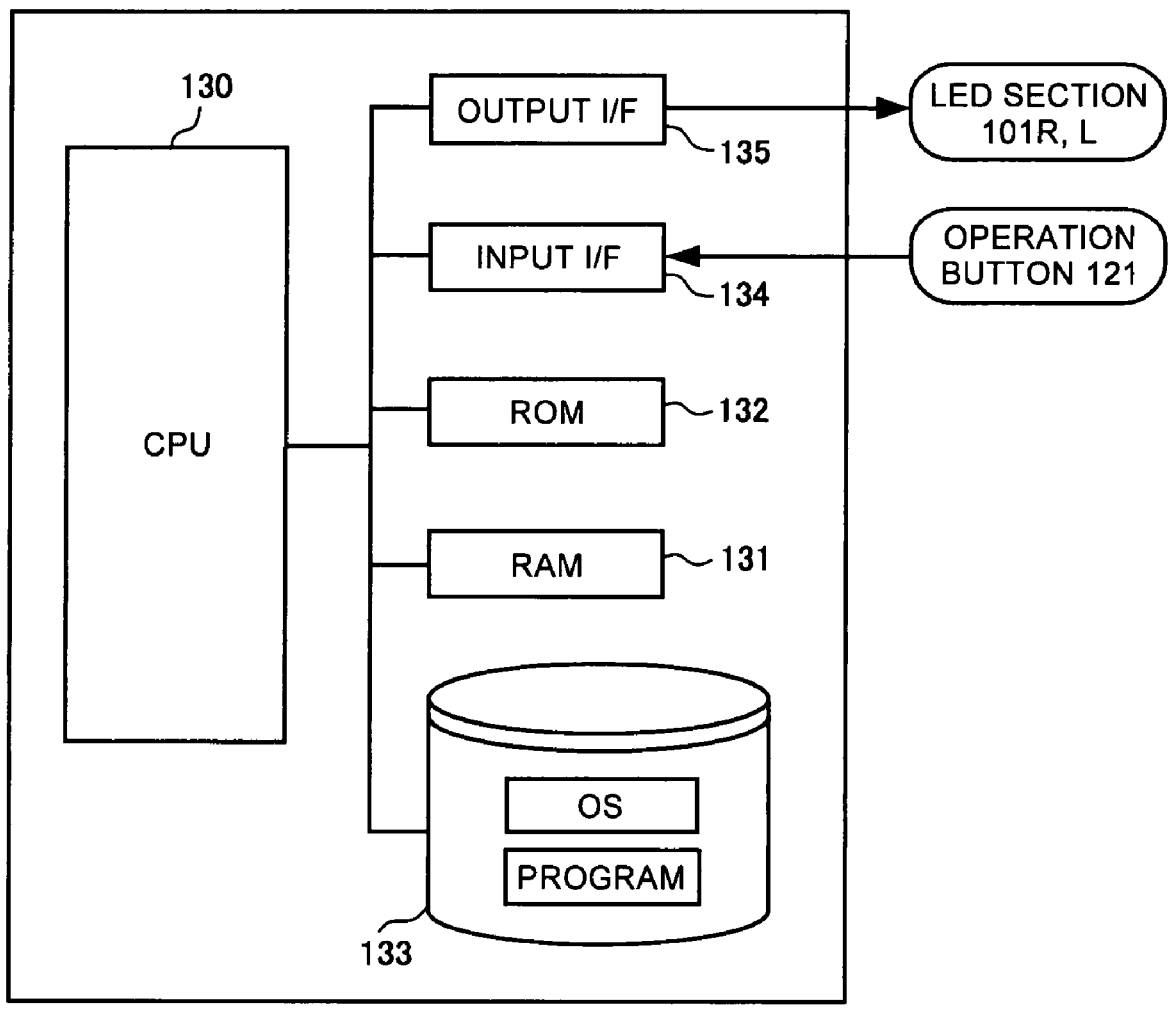
FIG. 13 is a diagram showing the configuration of the controller for the fatigue relief supporting apparatus according to the second embodiment.

As shown in FIG. 13, the controller 120 has a CPU 130 that controls the operation of the whole controller 120, a RAM 131 and a ROM 132 that are examples of memories, and magnetic storage device 133, an input interface 134 via which an operation signal from the operation button 121 is input, and an output interface 135 for the right-eye LED section 101R and left-eye LED section 101L. An operation system (OS) is installed in the magnetic storage device 133.

The controller 120 has a predetermined computer program pre-installed in its ROM 132 so as to operate as the fatigue relief supporting apparatus B of the present invention.

The predetermined computer program allows the controller 120, connected to the right-eye LED section 101R and left-eye LED section 101L, to function as LED control means for generating a light emission signal that allows the plurality of LEDs 102, constituting each of the LED sections 101R and 101L, to emit light so that a light image obtained by allowing the plurality of LEDs 102 to sequentially emit light shuttles in the horizontal direction with respect to the user and allowing the plurality of LEDs 102, constituting each of the LED sections 101R and 101L, to emit light on the basis of the generated light emission signal, and as storage means for storing light emission signal patterns. The computer program allows the light image displayed on the LED sections 101R and 101L to have function that relieves his or her fatigue if the user looks down to follow the light image with the user's.

Figure 14:
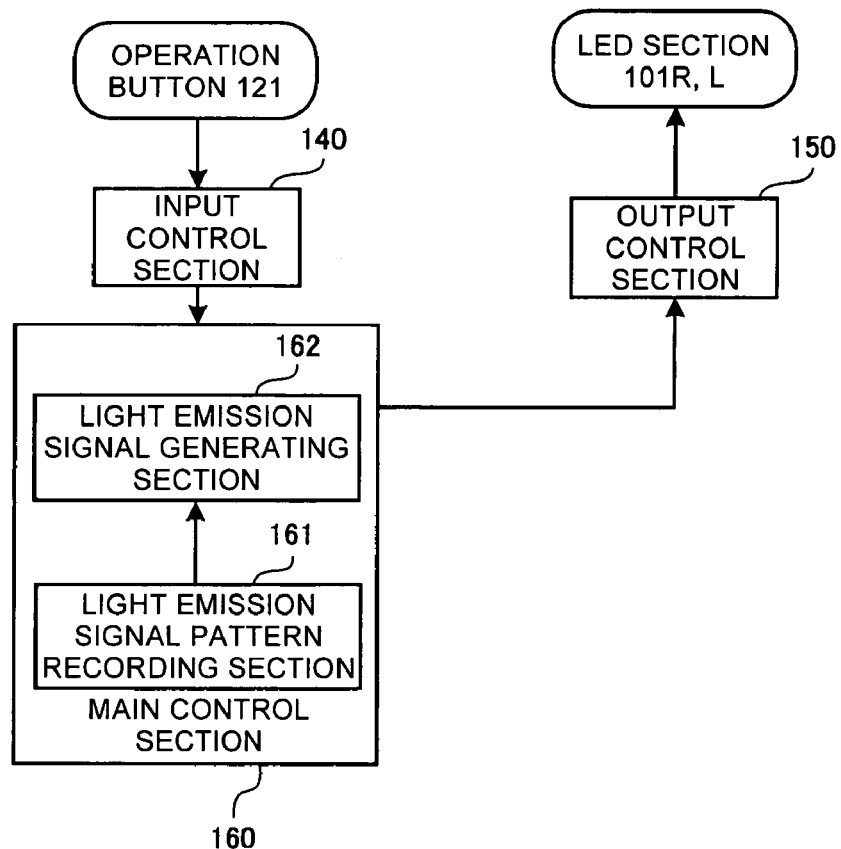
FIG. 14 is a diagram showing the configuration of the fatigue relief supporting apparatus according to the second embodiment.

In the present embodiment, the installed computer program is read in the RAM 131 and executed by the CPU 130 to form the functions shown in FIG. 14, on the controller 120. Specifically, the functions of an input control section 140, an output control section 150, and a main control section 160 are formed to constitute the fatigue relief supporting apparatus B.

The input control section 140 executes control to accept an input via the operation button 121 and to provide it to the main control section 160.

If a light emission signal described below is generated, the output control section 150 outputs it to the LED sections 101R and 101L.

The main control section 160 integrally controls the whole fatigue relief supporting apparatus B. The input control section 140 and output control section 150 operate under the control of the main control section 160.

The main control section 160 generates a light emission signal. Specifically, the main control section 160 has a light emission signal pattern recording section 161 that records light emission signal patterns allowing the plurality of LEDs 102 to emit light, in a predetermined area of predetermined data recording means (not shown), and a light emission signal generating section 162 that reads out any of the light emission signal patterns recorded in the light emission signal recording section 161 to generate a light emission signal.

Data on predetermined light emission signal patterns is recorded in the light emission signal pattern recording section 161.

In the present embodiment, two light emission signal patterns "Low" and "High" are recorded. The "Low" light emission signal pattern is configured so that a light image obtained by allowing the plurality of LEDs 102, constituting the LED sections 1011R and 101L, to emit light moves more slowly than that obtained in the case of the "High" light emission signal pattern. In the description of the present embodiment, these two light emission signal patterns are recorded. However, any number of types of light emission signal patterns may be recorded. The more number of light emission signal patterns recorded, the more number of choices for a light emission signal. This allows user to choose a light image that suits his or her taste and mood.

In the present embodiment, the data on the light emission signal patterns is installed in the magnetic storage device 133 of the controller 120 simultaneously with the installation of the above computer program in the magnetic storage device 133.

The light emission signal generating section 162 generates, on the basis of the light emission signal patterns, a light emission signal allowing the plurality of LEDs 102, constituting the LED sections 101R and 101L, to emit light.

A light image is obtained by allowing the plurality of LEDs 102, constituting the LED sections 101R and 101L, to sequentially emit light on the basis of a light emission signal generated by the light emission signal generating section 162. The light image shuttles in the horizontal direction of the LED sections 101R and 101L, that is, in the horizontal direction with respect to the user when the fatigue relief supporting apparatus B is worn on the user's head. The user looks down to follow the light image with his or her eyes to relieve his or her fatigue.

Further, like the object image in the fatigue relief supporting apparatus A according to the first embodiment, the light image according to this embodiment makes a change that promotes the user to blink. The light emission signal generating section 162 has a timer (not shown) that enables a light emission signal to be generated even after a predetermined time has elapsed.

In the present embodiment, the light image displayed on the LED sections 101R and 101L is configured to shuttle in the longitudinal direction of the LED sections 101R and 101L at a predetermined speed as is the case with the first embodiment.

That is to say, the plurality of LEDs 102 of the left-eye LED section 101L are allowed to sequentially emit light from the side of the left-eye LED section 101L where the temple 111 is provided, toward the right-eye LED section 101R. The plurality of LEDs 102 of the right-eye LED section 101R are then allowed to sequentially emit light from the left-eye LED section 101L toward the side of the right-eye LED section 101R where the temple 111 is provided. Subsequently, the plurality of LEDs 102 of the right-eye LED section 101R are allowed to sequentially emit light from the side of the right-eye LED section 101R where the temple 111 is provided, toward the left-eye LED section 101L. The plurality of LEDs 102 of the left-eye LED section 101L are then allowed to sequentially emit light from the right-eye LED section 101R toward the side of the left-eye LED section 101L where the temple 111 is provided. This light emission pattern is repeated to shuttle the light image in the horizontal direction of the LED sections 101R and 101L.

When light is emitted by the LED 102 located at the end of each LED section 101R or 101L where the temple 111 is provided, this LED 102 blinks a predetermined number of times.

The operation procedure of the fatigue relief supporting apparatus B is similar to that of the fatigue relief supporting apparatus A according to the above first embodiment.

A method for using the light image displayed on the LED sections 101R and 101L is similar to that according to the first embodiment. That is to say, the user follows the light image displayed on the LED sections 101R and 101L. Further, the user is promoted to blink in conjunction with blinking of the light image.

The user can thus relieve his or her fatigue by watching the light image displayed on the LED sections 101R and 101L through downcast eyes.

The fatigue relief supporting apparatus B according to the present embodiment is composed using the white LEDs 102. However, the present invention is not limited to this. For example, red or orange LEDs may be used. LEDs in plural colors may also be used.

Third Embodiment

A fatigue relief supporting apparatus C according to the present embodiment is configured in substantially the same manner as that in which the fatigue relief supporting apparatus B according to the second embodiment is configured. The fatigue relief supporting apparatus C is also used in the same manner as that in which the fatigue relief supporting apparatus B is used. However, the fatigue relief supporting apparatus C is different from the fatigue relief supporting apparatus B in that the former includes a right-eye optical fiber section 201R and a left-eye optical fiber section 201L each having a plurality of optical fibers 202, in place of the right-eye LED section 101R and left-eye LED section 101L. Specifically, the fatigue relief supporting apparatus C according to the present embodiment displays a light image obtained by allowing the optical fiber sections 201R and 201L to emit light, instead of a light image obtained by allowing the LED sections 101R and 101L to emit light.

Figure 15:
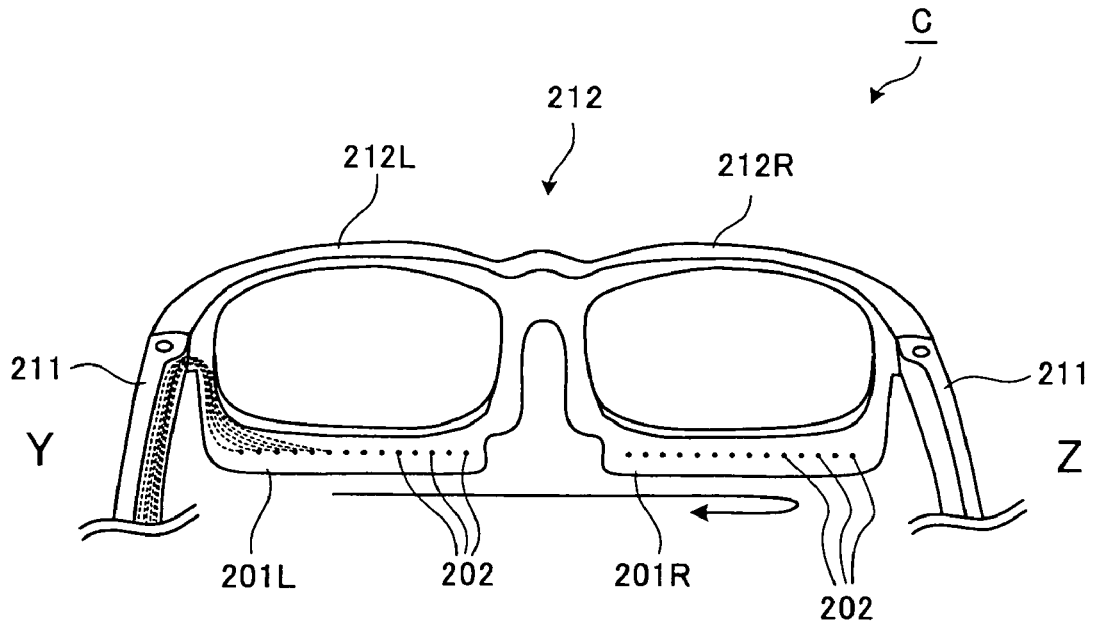
FIG. 15 is a partly sectional view showing the configuration of an optical fiber section of a fatigue relief supporting apparatus according to a third embodiment.

As shown in FIG. 15, the right-eye optical fiber section 201R and left-eye optical fiber section 201L consist of tip parts of a plurality of optical fibers 202 at their first ends arranged and set in lower frames of a right-eye frame 212R and a left-eye frame 212L, respectively, in a longitudinal direction of the lower frames. The tip parts of the plurality of optical fibers 202 at their first ends are set in the lower frames so as to be visible to the user when the fatigue relief supporting apparatus C is fixedly worn on the user's head. In the present embodiment, the right-eye optical fiber section 201R and left-eye optical fiber section 201L become clearly visible for user only when said user moves his or her eyes down at an angle equal to 45 degrees, as is the case with the fatigue relief supporting apparatus B according to the second embodiment.

Further, as shown in FIG. 15, the plurality of optical fibers 202 are embedded in a frame 212 and temples 211. The tip parts of the optical fibers 202 at their second ends are connected to a predetermined light source (not shown).

The light source allows the tip parts of the plurality of optical fibers 202 at their first ends to emit light. Furthermore, the light source is connected to a controller attached to the temple 211 at a predetermined position.

The controller is provided with an operation button, a power supply switch, and an end button, as is the case with the second embodiment.

The operation button according to the present embodiment allows the user to select one of a plurality of light emission signal patterns recorded in a light emission signal pattern recording section 261 described later. The present embodiment provides two operation buttons; one of the buttons is shown as "H", whereas the other button is shown as "L". The "H" button is associated with a "High" light emission signal pattern described later. The "L" button is associated with a "Low" light emission signal pattern described later.

Figure 16:
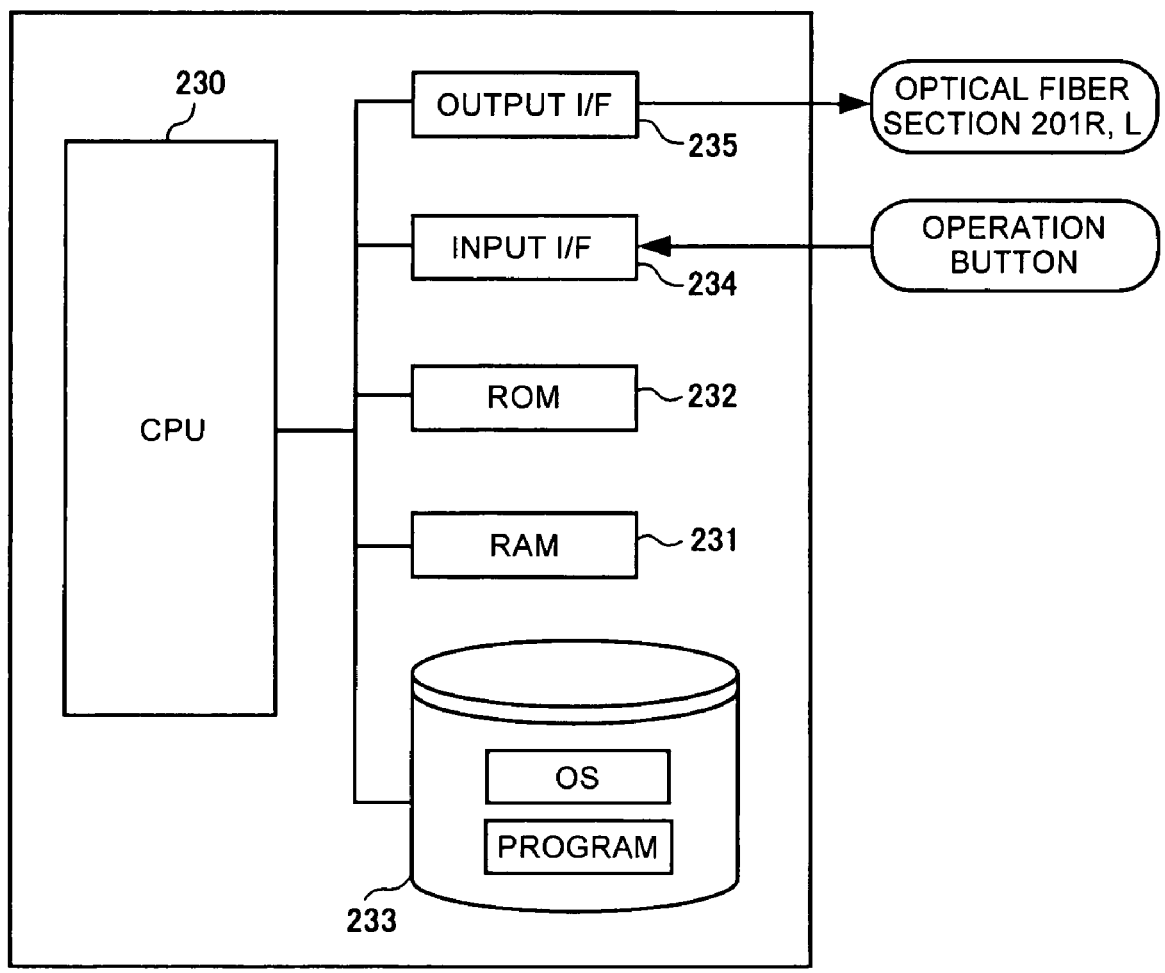
FIG. 16 is a diagram showing the configuration of a controller for the fatigue relief supporting apparatus according to the third embodiment.

As shown in FIG. 16, the controller has a CPU 230 that controls the operation of the whole controller, a RAM 231 and a ROM 232 that are examples of memories, and magnetic storage device 233, an input interface 234 via which an operation signal from the operation button is input, and an output interface 235 for the right-eye optical fiber section 201R and left-eye optical fiber section 201L. An operation system (OS) is installed in the magnetic storage device 233.

The controller has a predetermined computer program pre-installed in its ROM 232 so as to operate as the fatigue relief supporting apparatus C of the present invention.

Figure 17:
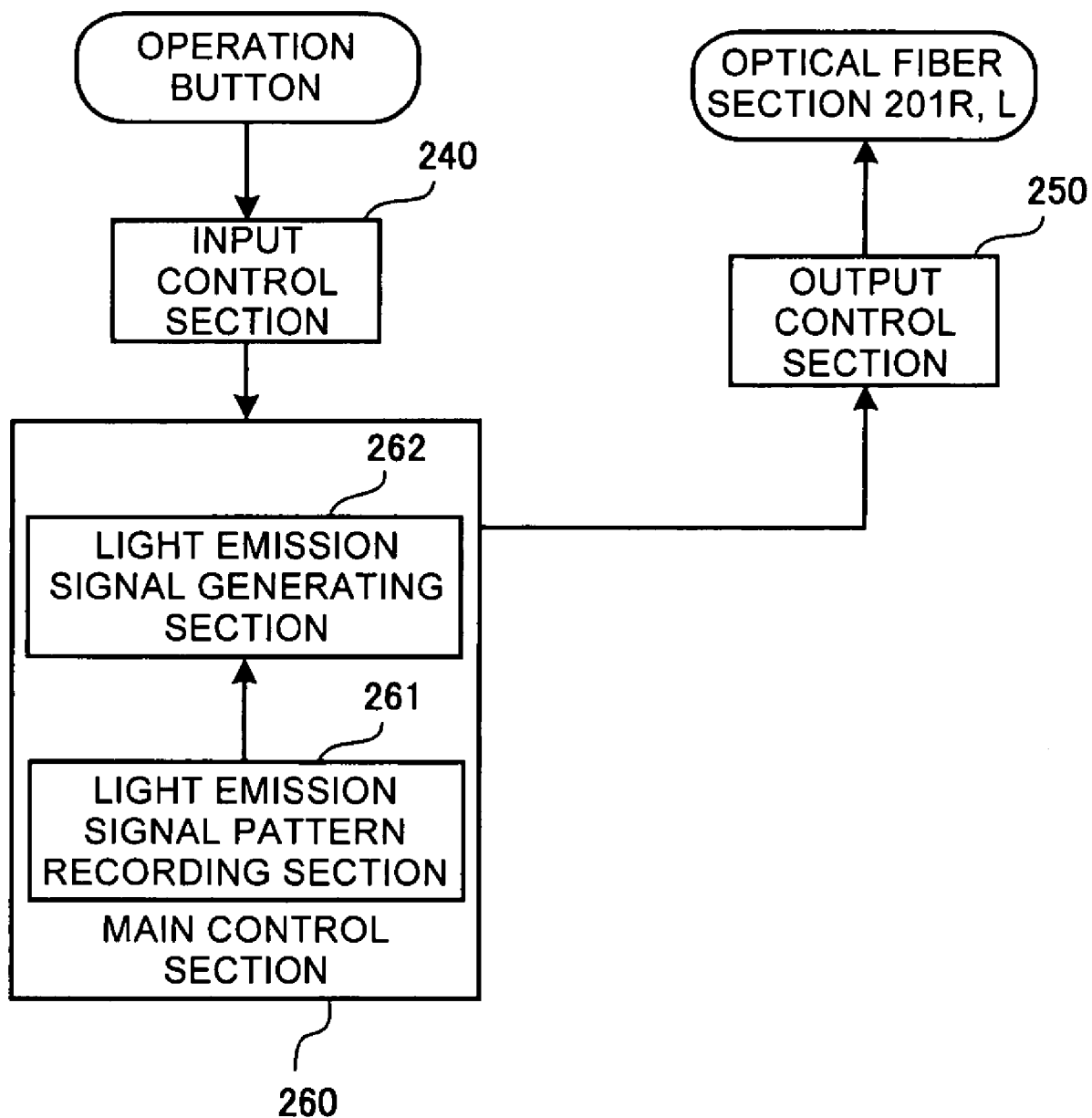
FIG. 17 is a diagram showing the configuration of the fatigue relief supporting apparatus according to the third embodiment.

The predetermined computer program allows the controller, connected to the right-eye optical fiber section 201R and left-eye optical fiber section 201L, to function as light emission signal generating means for generating a light emission signal that allows the plurality of optical fibers 202, constituting each of the optical fiber sections 201R and 201L, to emit light so that a light image obtained by allowing the plurality of optical fibers 202 to sequentially emit light shuttles in the horizontal direction with respect to the user and allowing the plurality of optical fibers 202, constituting each of the optical fiber sections 201R and 201L, to emit light on the basis of the generated light emission signal, and as storage means for storing light emission signal patterns. The computer program allows the light image to have a function that relieves his or her fatigue if the user looks down to follow the light image displayed on the optical fiber sections 201R and 201L with the user's In the present embodiment, the installed computer program is read in the RAM 231 and executed by the CPU 230 to form the functions shown in FIG. 17, on the controller. Specifically, the functions of an input control section 240, an output control section 250, and a main control section 260 are formed to constitute the fatigue relief supporting apparatus C.

The input control section 240 executes control to accept an input via the operation button and to provide it to the main control section 260.

When a light emission signal described below is generated, the output control section 250 outputs it to the optical fiber sections 201R and 201L.

The main control section 260 integrally controls the whole fatigue relief supporting apparatus C. The input control section 240 and output control section 250 operate under the control of the main control section 260.

The main control section 260 generates a light emission signal. Specifically, the main control section 260 has a light emission signal pattern recording section 261 that records light emission signal patterns allowing the plurality of optical fibers 202 to emit light, in a predetermined area of data recording means (not shown), and a light emission signal generating section 262 that reads out any of the light emission signal patterns recorded in the light emission signal pattern recording section 261 to generate a light emission signal.

Data on predetermined light emission signal patterns is recorded in the light emission signal pattern recording section 261.

In the present embodiment, two light emission signal patterns "Low" and "High" are recorded. The "Low" light emission signal pattern is configured so that a light image obtained by allowing the plurality of optical fibers 202, constituting the optical fiber sections 201R and 201L, to emit light moves more slowly than that obtained in the case of the "High" light emission signal pattern. In the description of the present embodiment, these two light emission signal patterns are recorded. However, any number of types of light emission signal patterns may be recorded.

In the present embodiment, the data on the light emission signal patterns is installed in the magnetic storage device 233 of the controller simultaneously with the installation of the above computer program in the magnetic storage device 233.

The light emission signal generating section 262 generates, on the basis of the light emission signal pattern, a light emission signal allowing the plurality of optical fibers 202, constituting the optical fiber sections 201R and 201L, to emit light.

A light image is obtained by allowing the plurality of optical fibers 202, constituting the optical fiber sections 201R and 201L, to sequentially emit light on the basis of a light emission signal generated by the light emission signal generating section 262. The light image shuttles in the horizontal direction of the optical fiber sections 201R and 201L, that is, in the horizontal direction with respect to the user when the fatigue relief supporting apparatus C is worn on the user's head. The user looks down to follow the light image with his or her eyes to relieve his or her fatigue.

Further, like the object image in the fatigue relief supporting apparatus B according to the second embodiment, the light image according to this embodiment makes a change that promotes the user to blink. The light emission signal generating section 262 has a timer (not shown) that enables a light emission signal to be generated even after a predetermined time has elapsed.

In the present embodiment, the light image displayed on the optical fiber sections 201R and 201L is configured to shuttle in the longitudinal direction of the optical fiber sections 201R and 201L at a predetermined speed as is the case with the second embodiment.

That is to say, the plurality of optical fibers 202 of the left-eye optical fiber section 201L are allowed to sequentially emit light from the side of the left-eye optical fiber section 201L where the temple 211 is provided, toward the right-eye optical fiber section 201R. The plurality of optical fibers 202 of the right-eye optical fiber section 201R are then allowed to sequentially emit light from the left-eye optical fiber section 201L toward the side of the right-eye optical fiber section 201R where the temple 211 is provided. Subsequently, the plurality of optical fibers 202 of the right-eye optical fiber section 201R are allowed to sequentially emit light from the side of the right-eye optical fiber section 201R where the temple 211 is provided, toward the left-eye optical fiber section 201L. The plurality of optical fibers 202 of the left-eye optical fiber section 201L are then allowed to sequentially emit light from the right-eye optical fiber section 201R toward the side of the left-eye optical fiber section 201L where the temple 211 is provided. This light emission pattern is repeated to shuttle the light image in the horizontal direction of the optical fiber sections 201R and 201L.

Further, when light is emitted by the optical fiber 202 located at the end of each optical fiber section 201R or 201L where the temple 211 is provided, this optical fiber 202 blinks a predetermined number of times.

The operation procedure and usage method of the fatigue relief supporting apparatus C are similar to those of the fatigue relief supporting apparatus B according to the above second embodiment.

The user can thus relieve his or her fatigue by watching the image light displayed on the optical fiber section 201 through downcast eyes.

The invention claimed is:

1. A fatigue relief supporting apparatus comprising:
   a main body that can be worn on a user's head; and
   a display member for displaying a predetermined object image, said display member being provided on or in said main body in such a manner that the display member is not clearly visible for said user when said user wearing said main body on his or her head looks straight ahead, and that the display member becomes clearly visible for said user when said user moves his or her eyes down,
   wherein the apparatus enables said user to see through the apparatus when said user wearing said main body on user's head looks straight ahead,
   wherein the apparatus has image generating means for generating the object image so as to shuttle in a horizontal direction with respect to the user and for displaying the generated object image on the display member,
   wherein, when the main body is worn on the user's head, the display member is disposed below a line joining the user's eyes, and
   wherein the object image has a function that if the user looks down to follow the object image with the user's eyes, his or her fatigue is relieved.

2. A fatigue relief supporting apparatus comprising:
   a main body that can be worn on a user's head; and
   a light emitting section having a plurality of light emitting members arranged in a line, said light emitting section being provided on or in said main body in such a manner that the light emitting section is not clearly visible for said user when said user wearing said main body on his or her head looks straight ahead, and that the light emitting section becomes clearly visible for said user when said user moves his or her eyes down,
   wherein the apparatus enables said user to see through the apparatus when said user wearing said main body on user's head looks straight ahead,
   wherein the apparatus has light emission signal generating means for generating a light emission signal that allows the plurality of light emitting members to emit light so that a light image obtained by allowing the plurality of light emitting members to sequentially emit light shuttles in a horizontal direction with respect to the user and for allowing the plurality of light emitting members to emit light on the basis of the generated light emission signal,
   wherein, when the main body is worn on the user's head, the light emitting section is disposed below a line joining the user's eyes, and
   wherein the light image has a function that if the user looks down to follow the light image with the user's eyes, his or her fatigue is relieved.

3. The fatigue relief supporting apparatus according to claim 1, wherein the display member is provided in the main body so as to become clearly visible for said user only when said user moves his or her eyes down at an angle equal to or larger than 20 degrees.

4. The fatigue relief supporting apparatus according to claim 1, wherein the display member has a predetermined width and a predetermined length, and
   the object image shuttles in a longitudinal direction of the display member.

5. The fatigue relief supporting apparatus according to claim 1, wherein the image generating means generates the object image such that the object image makes a change that promotes the user to blink.

6. The fatigue relief supporting apparatus according to claim 1, wherein the image generating means generates the object image at a predetermined timing.

7. The fatigue relief supporting apparatus according to claim 1, wherein the display member includes a right-eye display member located below the user's right eye and a left-eye display member located below the user's left eye.

8. The fatigue relief supporting apparatus according to claim 1, wherein the main body is shaped like glasses.

9. The fatigue relief supporting apparatus according to claim 8, wherein the main body comprises glasses frames having lower frames, and
   the display member is provided on the lower frames of the glasses frames.

10. The fatigue relief supporting apparatus according to claim 2, wherein the light emitting section is provided in the main body so as to become clearly visible for said user only when said user moves his or her eyes down at an angle equal to or larger than 20 degrees.

11. The fatigue relief supporting apparatus according to claim 2, wherein the light emitting section has a predetermined width and a predetermined length, and
   the light image shuffles in a longitudinal direction of the light emitting section.

12. The fatigue relief supporting apparatus according to claim 2, wherein the light emission signal generating means generates the light image such that the light image makes a change that promotes the user to blink.

13. The fatigue relief supporting apparatus according to claim 2, wherein the light emission signal generating means generates the light image at a predetermined timing.

14. The fatigue relief supporting apparatus according to claim 2, wherein the light emitting section includes a right-eye light emitting section located below the user's right eye and a left-eye light emitting section located below the user's left eye.

15. The fatigue relief supporting apparatus according to claim 2, wherein the main body is shaped like glasses.

16. The fatigue relief supporting apparatus according to claim 15, wherein the main body comprises glasses frames having lower frames, and the light emitting section is provided on the lower frames of the glasses frames.

* * * * *